(12) United States Patent
Ross

(10) Patent No.: US 12,201,395 B2
(45) Date of Patent: *Jan. 21, 2025

(54) HEAD-WORN REMOTE INFORMATICS SYSTEM

(71) Applicant: Hourglass Medical LLC, Monticello, IL (US)

(72) Inventor: Jeremy B. Ross, Monticello, IL (US)

(73) Assignee: Hourglass Medical LLC, Monticello, IL (US)

( * ) Notice: Subject to any disclaimer, the term of this patent is extended or adjusted under 35 U.S.C. 154(b) by 57 days.

This patent is subject to a terminal disclaimer.

(21) Appl. No.: 18/166,675

(22) Filed: Feb. 9, 2023

(65) Prior Publication Data

US 2023/0181039 A1 Jun. 15, 2023

Related U.S. Application Data

(63) Continuation of application No. 16/537,992, filed on Aug. 12, 2019, now Pat. No. 11,602,274.

(Continued)

(51) Int. Cl.
*A61B 5/00* (2006.01)
*A42B 3/14* (2006.01)
*G16H 40/67* (2018.01)

(52) U.S. Cl.
CPC .......... *A61B 5/0022* (2013.01); *A42B 3/142* (2013.01); *A61B 5/6803* (2013.01); *G16H 40/67* (2018.01); *A61B 2562/0219* (2013.01); *H04Q 2209/00* (2013.01); *H04Q 2209/10* (2013.01); *H04Q 2209/40* (2013.01)

(58) Field of Classification Search
CPC ....... A61B 5/00; A61B 5/0002; A61B 5/0004; A61B 5/0015; A61B 5/0022; A61B 5/6801; A61B 5/6802; A61B 5/6803; A61B 5/683; A61B 5/6831; A61B 5/6832; A61B 2562/0219; G16H 40/67; A42B 3/142; H04Q 9/00; H04Q 2209/00; H04Q 2209/10; H04Q 2209/40; H04Q 2209/43; H04Q 2209/70; H04Q 2209/80; H04Q 2209/82;

(Continued)

(56) References Cited

U.S. PATENT DOCUMENTS 7,610,637 B2   11/2009   Menkedick et al.
9,630,028 B2   4/2017    Browning et al.
(Continued)

FOREIGN PATENT DOCUMENTS

CN   107594732 A    1/2018
DE   202006013747 U1   12/2006
(Continued)

OTHER PUBLICATIONS

Bleda; et al., "Electrical Cardiac Monitoring in the Head for Helmet Applications", Computing in Cardiology (2015), 42:413-416.

(Continued)

*Primary Examiner* — Franklin D Balseca
(74) *Attorney, Agent, or Firm* — Ascenda Law Group, PC

(57) ABSTRACT

An informatics system that can be head-worn under a helmet and used to provide a wearer's vital statistics and other information to a remote monitoring station, for example in connection with pre-hospital emergency care.

13 Claims, 6 Drawing Sheets

Related U.S. Application Data

(60) Provisional application No. 62/721,158, filed on Aug. 22, 2018.

(58) Field of Classification Search
CPC ......... H04Q 2209/826; H04Q 2209/84; H04Q 2209/88
See application file for complete search history.

(56) References Cited

U.S. PATENT DOCUMENTS

| | | | |
|---|---|---|---|
| 9,642,412 | B2 | 5/2017 | Klotz et al. |
| 9,775,396 | B1 * | 10/2017 | Olivares Velasco ......................... H04B 1/3833 |
| 9,894,953 | B2 * | 2/2018 | Szalkowski ............ A42B 3/085 |
| 9,949,522 | B2 | 4/2018 | Ketterer et al. |
| 10,080,394 | B2 | 9/2018 | Johnston |
| 10,311,712 | B2 | 6/2019 | Jurkuvenas et al. |
| 10,667,731 | B2 * | 6/2020 | Everman ............ A61B 5/02433 |
| 11,253,771 | B2 * | 2/2022 | Vito ......................... A42B 3/20 |
| 11,602,274 | B2 * | 3/2023 | Ross .................... A61B 5/0002 |
| 2013/0060168 | A1 | 3/2013 | Chu et al. |
| 2013/0074248 | A1 | 3/2013 | Evans et al. |
| 2014/0296669 | A1 | 10/2014 | Gertsch et al. |
| 2017/0000417 | A1 | 1/2017 | Zhavoronkov et al. |
| 2017/0042272 | A1 | 2/2017 | Ferguson |
| 2017/0331614 | A1 * | 11/2017 | Vartiovaara ........... H04J 3/0673 |
| 2018/0092424 | A1 * | 4/2018 | Hall ........................ A42B 3/142 |
| 2018/0221682 | A1 | 8/2018 | Pepitone et al. |
| 2019/0191813 | A1 | 6/2019 | Liu et al. |

FOREIGN PATENT DOCUMENTS

| | | | | |
|---|---|---|---|---|
| JP | 2006188771 | A * | 7/2006 | ............. A42B 3/145 |
| KR | 20110077295 | A * | 7/2011 | ......... G01N 27/4162 |

OTHER PUBLICATIONS

International Search Report and Written Opinion mailed Nov. 7, 2019, from the ISA/European Patent Office, for International Patent Application No. PCT/US2019/046127 (filed Aug. 12, 2019), 14 pages.

Von Rosenberg; et al., "Smart Helmet: Monitoring Brain, Cardiac and Respiratory Activity", 37th Annual International Conference of the IEEE Engineering in Medicine and Biology Society (EMBC) (2015), pp. 1829-1832.

Von Rosenberg; et al., "Vital Signs From Inside a Helmet: A Multichannel Face-Lead Study", 2015 IEEE International Conference on Acoustics, Speech and Signal Processing (ICASSP) (Apr. 19-24, 2015), pp. 982-986.

* cited by examiner

HEAD-WORN REMOTE INFORMATICS SYSTEM

RELATED APPLICATIONS

This is a Continuation of U.S. application Ser. No. 16/537,992, filed Aug. 12, 2019, which is a Nonprovisional and claims the priority benefit of U.S. Provisional Application No. 62/721,158, filed Aug. 22, 2018, each of which is incorporated herein by reference.

FIELD OF THE INVENTION

The present invention provides an informatics system that can be head-worn under a helmet and used to provide a wearer's vital statistics and other information to a remote monitoring station, for example in connection with pre-hospital emergency care.

BACKGROUND von Rosenberg et al. reported on the need for rapid assessment of injuries, and especially head traumas, following road-traffic accidents and proposed an integrated system for monitoring cardiac activity as well as brain function inside of a motorcycle helmet. von Rosenberg, W. et al., "Smart Helmet: Monitoring Brain, Cardiac and Respiratory Activity," Conf. Proc. IEEE Eng. Med. Biol. Soc. 2015, pp. 1829-32 (2015). The proposed monitoring device included electrodes sewn in the helmet's lining at locations where they would come into contact with the wearer's skin when the helmet was worn. While such an arrangement allows for extracting vital signs and other information from an individual whilst the helmet is being worn, removal of the helmet results in loss of monitoring capability.

SUMMARY OF THE INVENTION

In various embodiments, an informatics system configured in accordance with the present invention is head-worn under a helmet and is operable to provide a wearer's vital statistics and other information to a remote monitoring station, for example in connection with pre-hospital emergency care. In one embodiment, the informatics system is included within or mounted to a harness that remains on a wearer's head after the helmet is removed. Thus, monitoring of the wearer's vital signs and other biometric information and telemetry are not interrupted by removal of the helmet.

In one embodiment, the informatics system includes a sensor package configured for monitoring of a wearer's vital statistics and a telemetry transmitter for transmitting a record of the wearer's vital statistics to a remote monitoring location. The informatics system is integrated within a helmet retention system that is adapted to be removably secured to a helmet, and the sensor package may include one or more sensor pads configured to contact a wearer at one or more points on the wearer's body. In some instances, the sensor pads are coupled to provide electrical signal inputs to a processor of the informatics system, and the processor is configured to sample the signals from the sensor pads periodically and to transmit a record of the sampled signals to the remote monitoring location via the telemetry transmitter. The processor may also be configured to store a record of the sampled signals in a writable memory of the informatics system. Optionally, a power supply may be included within the helmet retention system, as may one or more accelerometers be so included and coupled to provide inputs to the processor.

A further embodiment of the invention provides a headband having a sensor arrangement configured for monitoring of a wearer's vital statistics. The sensor arrangement includes one or more sensor pads configured to contact a wearer at one or more points on the wearer's body. The sensor pads are coupled to provide electrical signal inputs to a processor of the sensor arrangement, and the processor is configured to sample the signals from the sensor pads periodically. The headband is wearable under a helmet such that removal of the helmet from the wearer will not cause removal of the sensor arrangement. In some cases, the headband is part of or is included in a helmet retention system adapted to be removably securable to the helmet, and the retention system may include a telemetry transmitter coupled to the processor. The helmet retention system may also include a power source for the sensor arrangement. Optionally, the sensor arrangement may include one or more accelerometers and/or writable memories coupled to the processor.

Another embodiment provides for a processor of a head-worn informatics system periodically sampling electrical signals provided by one or more sensor pads of the informatics system, which sensor pads are configured for electrophysiological monitoring of a wearer of the informatics system, and transmitting a record of the sampled signals to a monitoring facility remote from the informatics system via a telemetry transmitter of the informatics system, wherein even after subsequent removal of a helmet from the wearer, the processor continues to sample the electrical signals and transmit the record of the sampled signals to the monitoring facility. Removal of the helmet does not cause removal of the head-worn informatics system from the wearer. For example, removal of the helmet does not cause removal of a helmet retention system in which the head-worn informatics system is integrated from the wearer, nor does it cause removal of sensor package of the head-worn informatics system from the wearer, nor does it cause removal of a headband in which the sensor pads of the head-worn informatics system are integrated from the wearer.

Prior to removal of the helmet from the wearer of the head-worn informatics system, a primary power source may be dissociated from the head-worn informatics system, and the head-worn informatic system may then revert to using a secondary power source. Subsequent to removal of the helmet from the wearer of the head-worn informatics system and the head-worn informatic system reverting to using a secondary power source, primary power may be restored to the head-worn informatics system from a transportable power supply.

In addition to transmitting the record of the sampled signals, that record may also be stored in a memory of the head-worn informatics system. Also, inputs concerning rapid accelerations and/or decelerations of the wearer's head may be provided to a processor of the head-worn informatics system from one or more accelerometers of the head-worn informatics system.

BRIEF DESCRIPTION OF THE DRAWINGS

The present invention is illustrated by way of example, and not limitation, in the figures of the accompanying drawings, in which.

DETAILED DESCRIPTION

Described herein is an informatics system that can be head-worn under a helmet and used to provide a wearer's vital statistics and other information to a remote monitoring station, for example in connection with pre-hospital emergency care. In one embodiment, the informatics system is included within or mounted to a harness that remains on a wearer's head after the helmet is removed. Thus, monitoring of the wearer's vital signs and other biometric information and telemetry are not interrupted by removal of the helmet.

Figure 1:
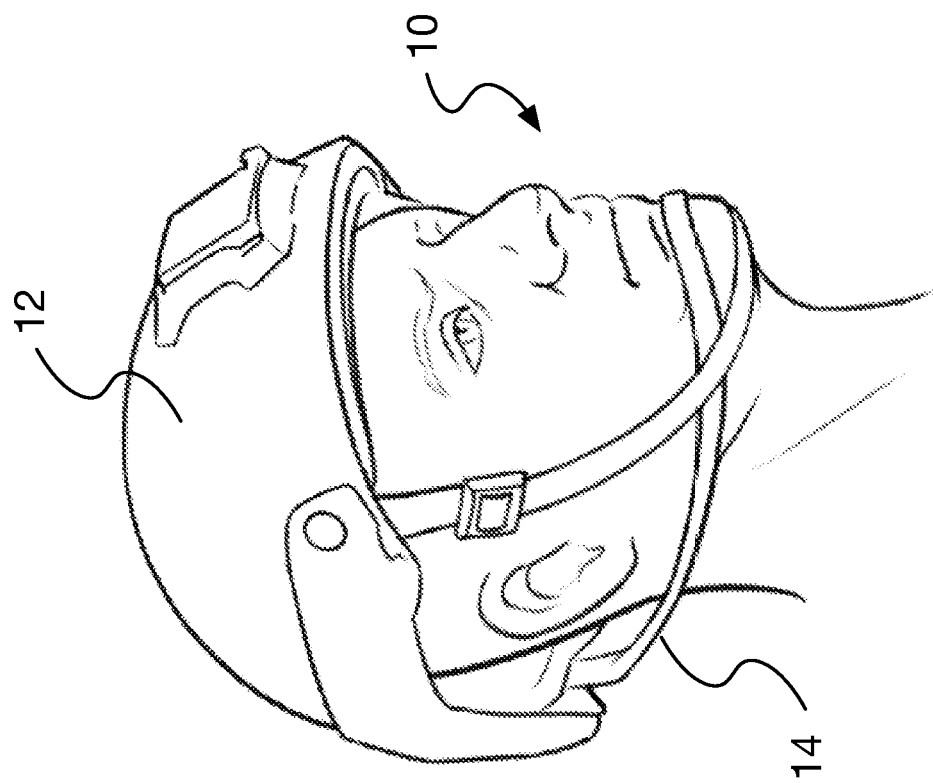
FIG. 1 illustrates an individual wearing a helmet under which a sensor package configured in accordance with embodiments of the present invention may be worn.

FIG. 1 illustrates an individual 10 wearing a helmet 12. The helmet is secured to the individual's head by means of a retention system 14. In this example, the retention system includes a plurality of straps that pass across the wearer's chin, either directly or with a chin guard, allowing the helmet to be positioned squarely on the wearer's head with the front of the helmet protecting the wearer's forehead and the back of the helmet positioned approximately adjacent the nape of the wearer's neck. The straps of the retention system are adjusted, typically using a ratchet system and/or one or more buckles, so that the helmet sits squarely and securely on the wearer's head with the straps just below and in front of the ears.

Figure 3:
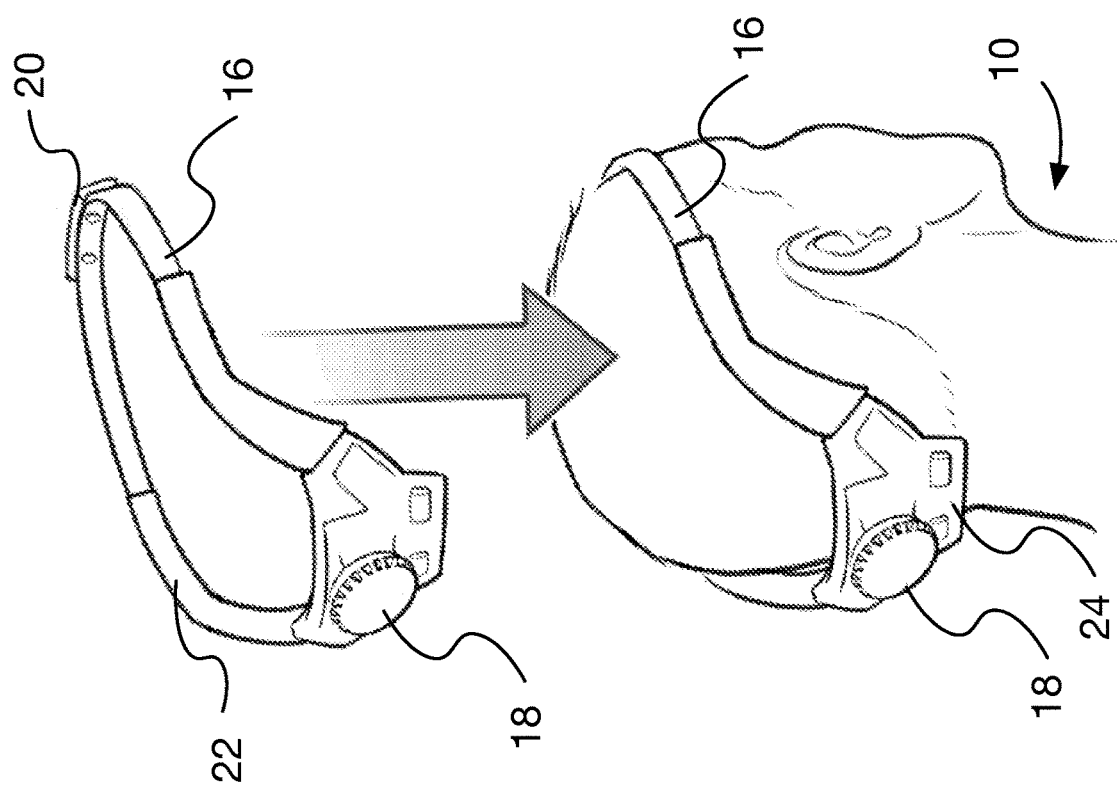
FIG. 3 illustrates how the headband section of the retention system shown in FIG. 2 fits over the wearer's head.
Figure 2:
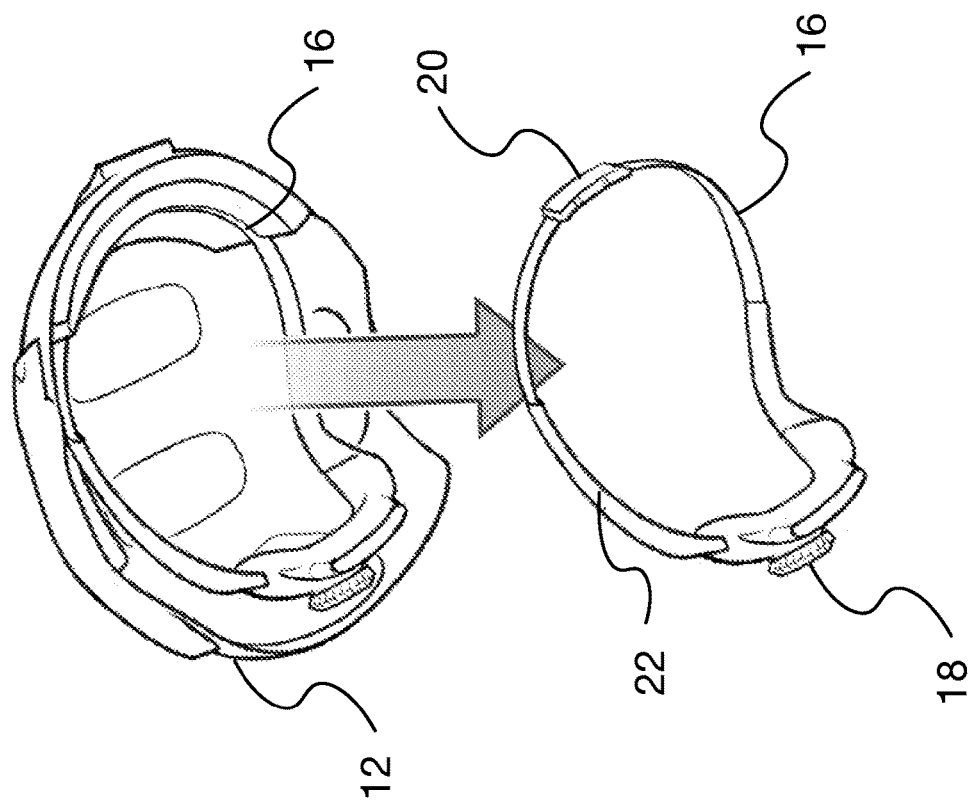
FIG. 2 shows an underside view of the helmet illustrated in FIG. 1, exposing a portion of a retention system in the form of a headband that is outfitted with a sensor package configured in accordance with embodiments of the present invention.

FIG. 2 shows an underside view of helmet 12 exposing a portion of the retention system 14 in the form of a headband 16. For clarity, the straps are not shown in this view. The straps may be removable from the retention system 14. FIG. 3 illustrates how the headband section 16 of the retention system 14 fits over the wearer's head.

As illustrated in these views, headband 16 is fitted over the wearer's head and sized using the dial/ratchet adjustment mechanism 18 located at the back of the headband. When headband 16 is secured within helmet 12, for example using snaps, hook and loop, or other fastening means, adjusting the fit of headband 16 using the ratchet will thus secure the helmet to the wearer's head. However, because the headband 16 is only removably secured within the helmet 12, the helmet 12 can be taken off of the wearer's head while leaving the headband 16 in place (as shown in FIG. 3).

Headband 16 includes a sensor package 20 that allows for monitoring of the wearer's vital statistics. A power source and telemetry transmitter 24 may be included in headband 16 and attached to the sensor package via one or more wire leads 22. Thus, even with the helmet removed, the sensor package 20 can continue to relay information concerning the wearer's vital statistics and other monitored biometrics via the telemetry transmitter, because headband 16 remains attached to the wearer.

Figure 4:
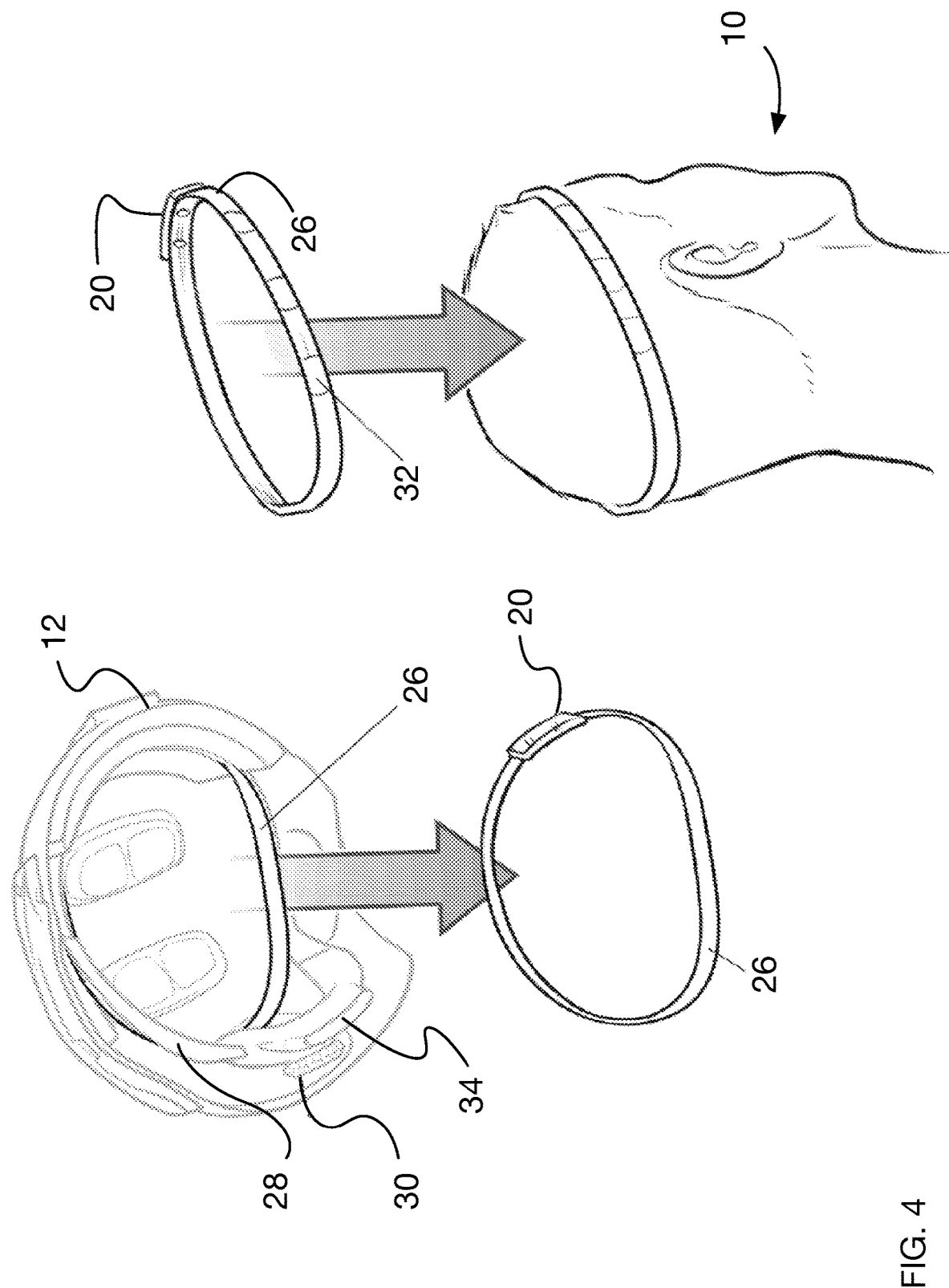
FIG. 4 shows an alternative embodiment in which a sensor package configured in accordance with embodiments of the present invention is mounted to an elastic or other sizeable strap that is wearable about an individual's head under a helmet.

FIG. 4 shows an alternative embodiment in which the sensor package 20 is mounted to an elastic or other sizeable strap 26 that is fittable about the wearer's head. In this embodiment, the strap 26 is not part of the helmet retention system per se, but instead is separately secured to an existing helmet retention system 28 associated with helmet 12. The helmet retention system 28 may include a ratchet/dial-like adjustment means 30 and the strap 26 may be secured to a harness portion of the helmet retention system using hook and loop fasteners 32, snaps, or other fastening means. Strap 26 includes integral wire leads (not shown in these views) that electrically connect sensor package 20 to a power source and telemetry transmitter 34 in the helmet retention system. In this embodiment, the strap 26 and sensor package may be temporarily removed from a wearer's head when the helmet is removed, quickly detached from the helmet retention system, and then replaced on the wearer's head. Although this will entail a brief period of time when the wearer's vital statistics, etc. are not being monitored through the sensor package, it nevertheless provides an effective means for near-continuous provision of same and effective pre-hospital emergency care monitoring.

Figure 6A:
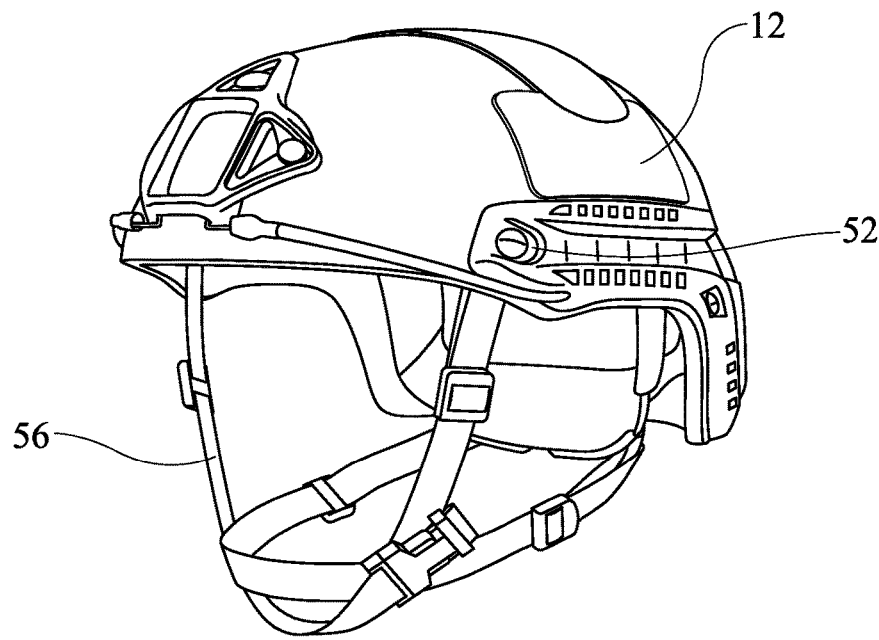
FIGS. 6A-6D illustrate yet a further embodiment, in which a helmet has an associated retention system that includes a plurality of straps, a headband arrangement that accommodates a sensor package configured in accordance with embodiments of the present invention secured to an interior of the helmet, and an associated ratchet tensioning system.
Figure 6B:
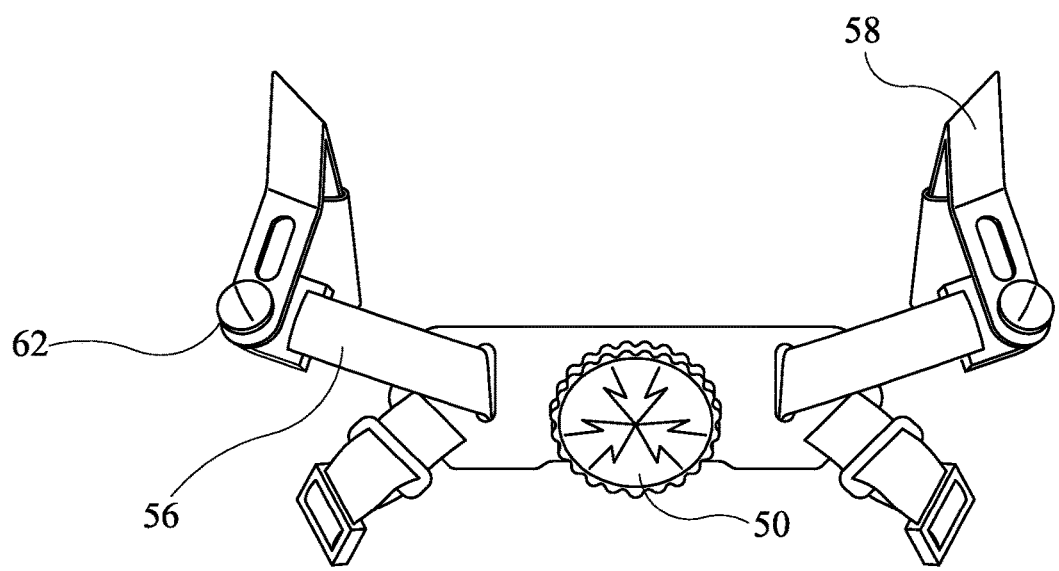
Figure 6C:
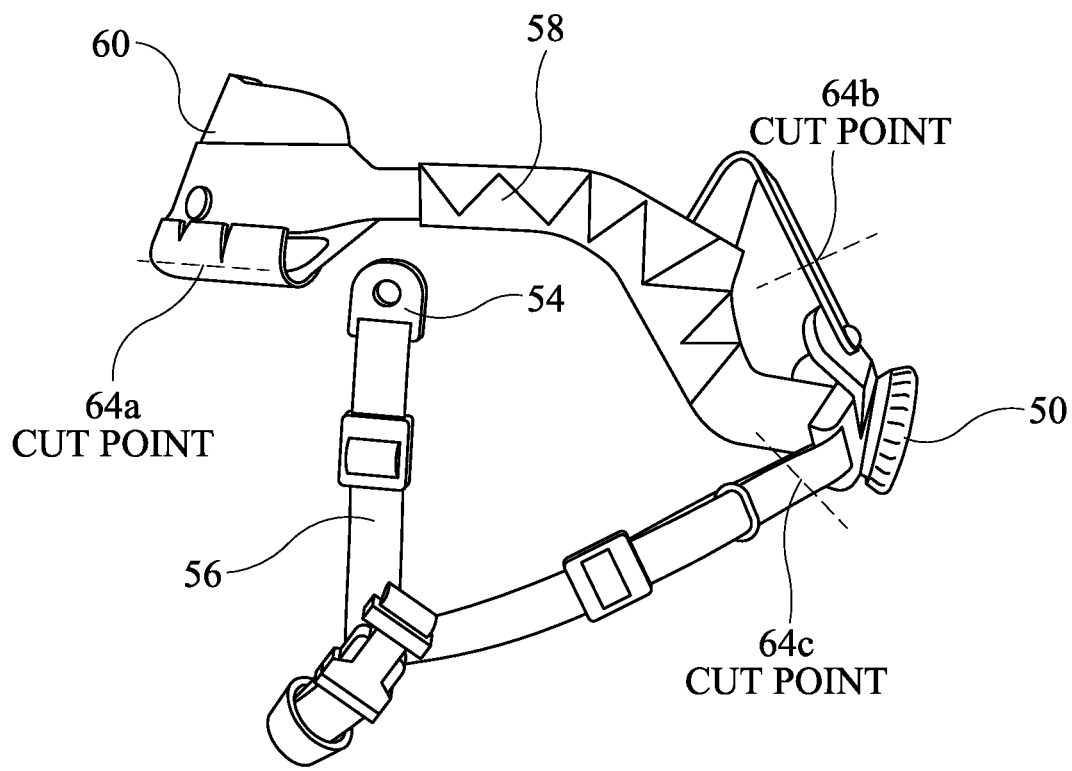

Yet a further embodiment is illustrated in FIGS. 6A-6C. In this example, a helmet 12 has an associated retention system that includes a plurality of straps (e.g., chin straps) 56, a headband arrangement 58 that is secured to an interior of the helmet, and an associated ratchet tensioning means 50. The straps are secured near the temple portion of helmet 12 by bolts 52 which pass through eyelets 54. By adjusting the ratchet 50, the headband arrangement 58 and/or the straps 56 are tightened or loosened, thereby fitting the helmet to the wearer's head. In accordance with the present invention, sensor arrangements 60, 62 are included in portions of the headband arrangement, for example near the forehead and behind the ears of the wearer. As with the above-described embodiments, a power source and telemetry transmitter may be included in headband arrangement and/or the ratchet tensioning means and attached to the sensor package(s) via one or more wire leads.

Figure 6D:
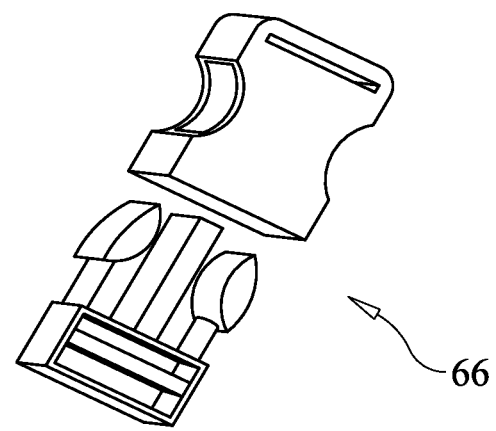

In this example, the helmet may be removed while leaving the headband arrangement and sensor package(s) in place by physically cutting the helmet off of the wearer at one or more points 64a-64c. For example, the headband arrangement may be severed at a cut point 64a near the forehead and at a cut point 64b behind the ears of the wearer. Straps 56 may be severed at a cut point 64c behind the head of the wearer, allowing the helmet to be fully removed. In this way, removal of the helmet will not cause removal of the sensor arrangement(s). Alternatively, one or more of the headband arrangement and/or straps may be filled with quick release buckles 66 (see FIG. 6D), pins, or other arrangement, to allow for removal of the helmet without the need to cut the straps, etc.

Figure 5:
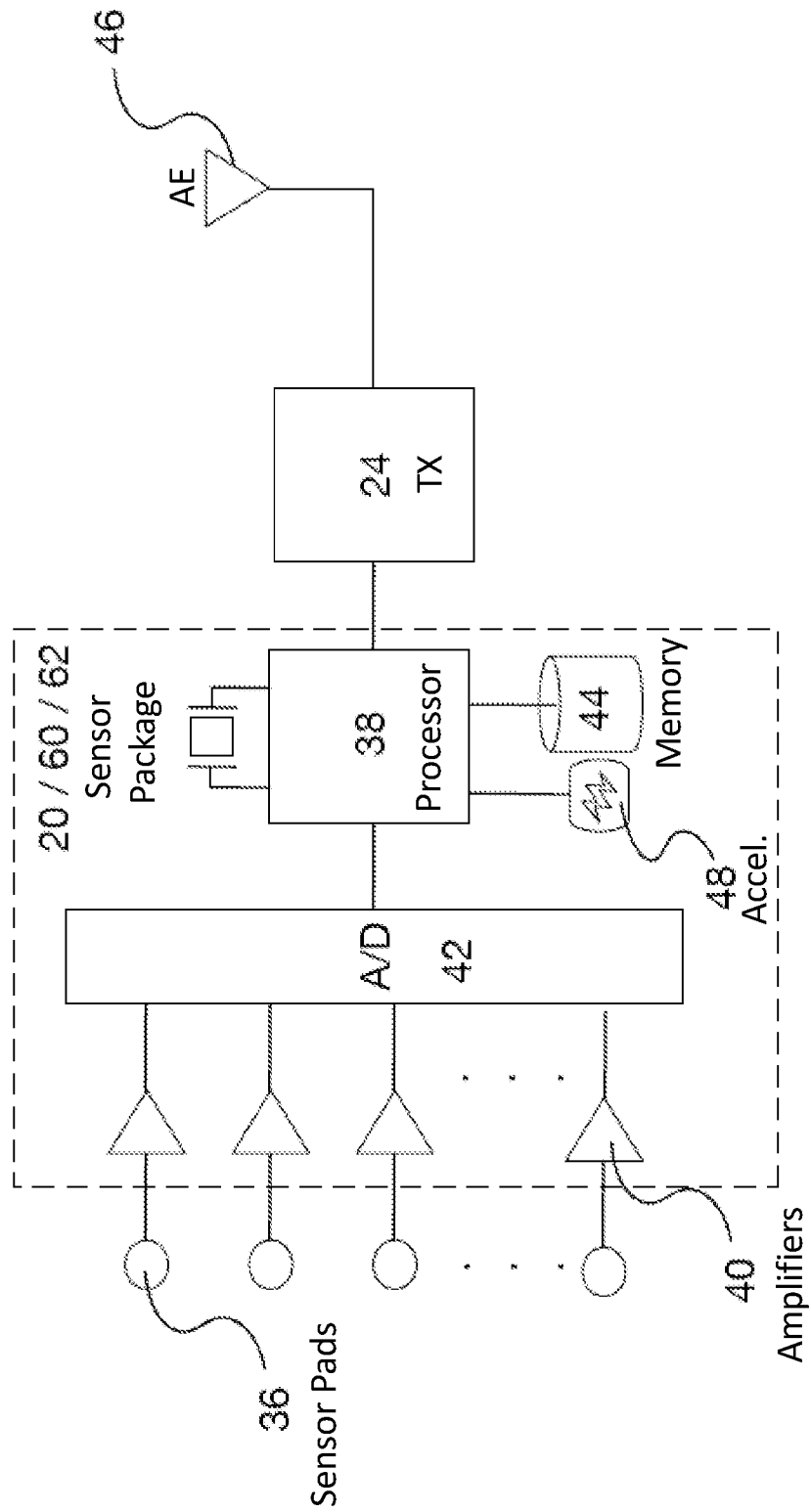
FIG. 5 shows details of sensor packages that may be included in a retention system of a helmet and/or headband wearable under a helmet in accordance with embodiments of the present invention.

As illustrated in FIG. 5, the sensor package(s) 20, 60, 62, included in the above-described embodiments may be electrically coupled to one or more sensor pads 36 constructed of conductive fabric that contact the wearer at the forehead and elsewhere (e.g., the nape of the neck, the temples, etc.).

One or more of the sensor pads may be integrated in the headband 16, 58. Alternatively, or in addition, sensor pads may be included in a plurality of straps to be positioned over the head of the wearer or in a cap-like garment worn under the helmet. This would allow for additional sensor readings for electrophysiological or other noninvasive monitoring of the wearer.

The sensor pads 36 and associated electronics may allow for detection of electrical signals in the manner described by von Rosenberg et al. For example, the sensor pads may be attached by electrical leads to a processor 38, e.g., via associated amplifiers 40, analog-to-digital converter 42, etc., which samples the signals from the sensor pads periodically. A record of the sampled signals may be stored locally at the helmet, e.g., in a suitable writable memory 44 such as a flash memory, and also may be transmitted to a remote monitoring location via the telemetry transmitter 24 and an associated antenna 46. Alternatively, the telemetry may be transmitted only when the transmitter is activated, e.g., by an on-scene paramedic, or by the wearer him/herself. Upon command, any stored samples may be similarly transmitted so that a history of the wearer's biometric and vital signs can be analyzed by a physician or other person at the remote monitoring station.

In some embodiments, the sensor package 20 may also include one or more accelerometers 48 which provide inputs to processor 38 concerning rapid accelerations/decelerations of the wearer's head. Such measurements may be important when assessing possible traumatic brain injuries, cervical spinal injuries, and the like.

Although not shown in this view, a power source for the electronics is provided and may be housed within the retention system or located external thereto (e.g., worn on a vest or pack). In some cases, a primary power source may be located external to the other components of the system and a secondary power source provided integral thereto. This would allow the primary power source to be decoupled from the system, which would then revert to using the secondary power source (e.g., a small battery or the like), at least temporarily. This would allow for continuous monitoring of the biometric and vital signs and provision of related telemetry. Primary power may later be restored by an attending medic using a transportable power supply. To facilitate this operation, the system may be provided with one or more ports allowing connection of different forms of power supplies.

Importantly, in embodiments of the invention, removal of the helmet does not dissociate the sensor pads and associated electronics from the wearer permanently. Thus, recording and telemetry of the wearer's vital statistics and other biometric information, e.g., via the sensor pads, does not stop when the helmet is removed.

What is claimed is:

1. A helmet, comprising: a retention system for securing to a head of a wearer, the retention system including a headband secured within the helmet and adjustable by a ratchet mechanism located at a back of the headband and a plurality of straps arranged so that when the helmet is worn pass across a chin of the wearer, the straps being adjustable by one or more buckles, wherein the helmet is configured so that, when worn, a front of the helmet protects a forehead of the wearer and a back of the helmet is adjacent a nape of a neck of the wearer, the helmet further including a sensor package configured with one or more sensor pads to monitor vital statistics of the wearer when the helmet is worn, a battery, and a telemetry transmitter, wherein the sensor package is detachably secured to the retention system by being positioned on a removable strap that is removably attached to the headband of the retention system.

2. The helmet of claim 1, wherein the straps are part of a harness adjustable by the ratchet mechanism.

3. The helmet of claim 1, wherein the one or more sensor pads are arranged to contact a body of the wearer at one or more points on the wearer's body and coupled to input electrical signals to a processor of the sensor package, the processor being configured to sample the electrical signals input from the one or more sensor pads periodically and to transmit a record of the sampled electrical signals input from the one or more sensor pads to a remote monitoring location via the telemetry transmitter.

4. The helmet of claim 3, wherein said processor is further configured to store the record of the sampled electrical signals input from the one or more sensor pads in a writable memory of the sensor package.

5. The helmet of claim 1, wherein the sensor package includes an accelerometer and the one or more sensor pads are configured to contact a body of the wearer at one or more points on the wearer's body.

6. The helmet of claim 1, wherein the removable strap is an elastic strap and the sensor package is mounted on the elastic strap.

7. The helmet of claim 1, wherein the removable strap is a sizeable strap and the sensor package is mounted on the sizeable strap.

8. The helmet of claim 1, wherein the one or more sensor pads are arranged to contact a body of the wearer near the wearer's forehead when the helmet is worn by the wearer.

9. The helmet of claim 1, wherein the one or more sensor pads are arranged to contact a body of the wearer behind ears of the wearer when the helmet is worn by the wearer.

10. The helmet of claim 1, wherein the plurality of straps include cut points.

11. The helmet of claim 1, wherein the one or more sensor pads are constructed of conductive fabric and configured to contact a body of the wearer at one or more points on the wearer's body.

12. The helmet of claim 11, wherein the one or more sensor pads are coupled to input electrical signals to a processor of the sensor package, the processor being configured to sample the electrical signals input from the one or more sensor pads periodically and to transmit a record of the sampled electrical signals input from the one or more sensor pads to a remote monitoring location via the telemetry transmitter.

13. The helmet of claim 11, wherein the one or more sensor pads are coupled to input electrical signals to a processor of the sensor package, the processor being configured to sample the electrical signals input from the one or more sensor pads periodically and to store a record of the sampled electrical signals input from the one or more sensor pads in a writable memory of the sensor package.

* * * * *